United States Patent [19]

Nudelman et al.

[11] 4,197,240

[45] Apr. 8, 1980

[54] PENICILLIN DERIVATIVES

[75] Inventors: Abraham Nudelman, Rehovot; Abraham Patchornik, Ness-Ziyona, both of Israel

[73] Assignee: Yeda Research and Development Co. Ltd., Rehovot, Israel

[21] Appl. No.: 863,730

[22] Filed: Dec. 23, 1977

[51] Int. Cl.² .......................................... C07D 499/44
[52] U.S. Cl. ................................................. 260/239.1
[58] Field of Search ...................... 260/239.1; 424/271

[56] References Cited

U.S. PATENT DOCUMENTS

| | | | |
|---|---|---|---|
| 3,192,198 | 6/1965 | Nayler et al. | 260/239.1 |
| 3,966,710 | 6/1976 | McFarland et al. | 260/239.1 |
| 3,985,739 | 10/1976 | Dunn et al. | 260/243 C |
| 3,989,694 | 11/1976 | Berges | 260/243 C |
| 3,994,877 | 11/1976 | Erickson et al. | 260/239.1 |

*Primary Examiner*—Gerald A. Schwartz
*Attorney, Agent, or Firm*—William J. Stein; Eugene O. Retter; George W. Rauchfuss, Jr.

[57] ABSTRACT

New 7-[4-hydroxy-3-(substitutedmethyl)phenyl]acetamido penicillin derivatives are prepared which are useful as antibiotics.

10 Claims, No Drawings

PENICILLIN DERIVATIVES

FIELD OF INVENTION

This invention relates to new penicillin derivatives which are useful as antibiotics and the processes for their preparation.

SUMMARY OF INVENTION

The compounds of Formula 1 are useful as antibiotics

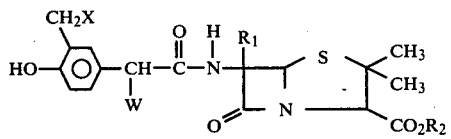

Formula 1 wherein W is hydrogen, hydroxy, —$SO_3H$ or —$COOR_3$ wherein $R_3$ is selected from hydrogen, phenyl or 5-indanyl, an alkanoyloxymethyl group in which the alkanoyloxy group contains from 2 to 5 carbon atoms, or a 1 to 4 carbon alkyl group; —$NHR_4$ wherein $R_4$ is hydrogen, tert-butyloxycarbonyl,

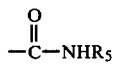

wherein $R_5$ is hydrogen, a lower alkyl group of from 1 to 4 carbon atoms or a phenyl group; X is chloro, bromo, an alkoxy group from 1 to 4 carbon atoms; an $R_6$—S—, $R_6SO$—, $R_6SO_2$— group wherein $R_6$ is a lower alkyl group of form 1 to 4 carbon atoms; azido; cyano; NCNH—; $HSO_3$—; —SCN; —OCN; $CH_3SO_2NH$—; isothiourea; substituted isothiourea wherein the substituents are amino, formylamino, guanylamino, a lower alkyl group of from 1 to 4 carbon atoms and concatenated alkylene groups in the form of a series of from 2 to 6 methylene groups; pyridylthio; 1-methyltetrazol-5-ylthio; 1,3,4-thiadiazol-2-ylthio; 1,3,4-triazol-2-ylthio; —SH; $SSO_3H$; $F_3CS$—;

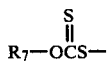

wherein $R_7$ is lower alkyl of from 1 to 4 carbon atoms;

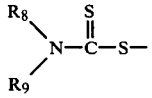

wherein $R_8$ and $R_9$ separately are hydrogen, a lower alkyl group of from 1 to 4 carbon atoms, when taken together $R_8$ and $R_9$ may form a concatenated chain of from 4 to 7 methylene groups, a concatenated chain of from 5 to 7 methylene groups wherein one of these methylene groups is replaced by an oxygen atom or an $R_{10}$—N group wherein $R_{10}$ is a lower alkyl group of from 1 to 4 carbon atoms, with a proviso that when X is chlorine or bromine $R_4$ is other than tert-butyloxycarbonyl. $R_1$ is hydrogen or a methoxy group. $R_2$ is hydrogen, a straight or branched lower alkyl group of from 1 to 4 carbon atoms, a straight or branched alkanoyloxymethyl group in which the alkanoyl moiety has from 1 to 4 carbon atoms, an alkanoylaminomethyl group in which the alkanoyl moiety is straight or branched and has from 1 to 4 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, p-(alkanoyloxy)benzyl group in which the alkanoyl moiety is straight or branched and has from 1 to 4 carbon atoms; an aminoalkanoyloxymethyl group in which the alkanoyl moiety has from 2 to 15 carbon atoms and the amino nitrogen may be mono- or di-substituted with a straight or branched lower alkyl group having from 1 to 4 carbon toms; and pharmaceutically acceptable salts thereof.

DETAILED DESCRIPTION OF THE INVENTION

In Formula 1 the substituent group represented by $R_2$ may be hydrogen.

In addition to hydrogen, $R_2$ may be a straight or branched alkyl group of from 1 to 4 carbon atoms. Or $R_2$ may be an alkanoyloxymethyl group represented by the formula

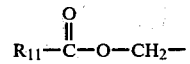

wherein $R_{11}$ is a straight or branched alkyl group of from 1 to4 carbon atoms. Additionally, $R_2$ may be an alkanoylaminomethyl or an alkoxycarbonylaminomethyl group represented by

wherein $R_{12}$ is a straight or branched alkyl group of from 1 to 4 carbon atoms or a straight or branched alkoxy group of from 1 to 4 carbon atoms and $R_{13}$ is hydrogen or a straight or branched alkyl group of form 1 to 4 carbon atoms. $R_2$ may be an alkanoyloxybenzyl group represented by the formula

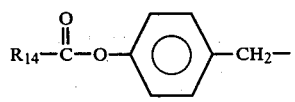

wherein $R_{14}$ is a straight or branched alkyl group of from 1 to 4 carbon atoms. $R_2$ may be an aminoalkanoyloxymethyl group represented by the formula

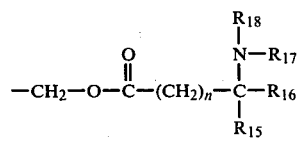

wherein n is 0 to 5, and each of $R_{15}$ and $R_{16}$ is selected from hydrogen or a straight or branched alkyl group of from 1 to 4 carbon atoms and each of $R_{17}$ and $R_{18}$ is selected from hydrogen or a straight or branched alkyl group of from 1 to 4 carbon atoms.

Illustrative examples of the straight or branched alkyl groups of from 1 to 4 carbon atoms which $R_2$ and $R_{11}$ to $R_{18}$, inclusive, may represent are: methyl, ethyl, n-propyl, isopropyl, n-butyl, isobutyl and tert-butyl.

Illustrative examples of the straight or branched alkoxy groups of from 1 to 4 carbon atoms which $R_{12}$ may represent are: methoxy, ethoxy, n-propoxy, isopropoxy, n-butoxy, sec-butoxy and tert-butoxy.

In Formula 1, the substituent group $R_1$ is hydrogen or methoxy.

Illustrative examples of the alkanoyl groups represented by $R_2$ are the following: acetyl, propionyl and butyryl.

In the Formula 1, W is hydrogen or hydroxyl. In addition, W is —$NHR_4$ wherein $R_4$ is hydrogen, an alkoxycarbonyl group in which the alkoxy moiety is straight or branched and has from 1 to 4 carbon atoms, a

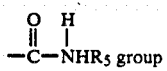
—$\overset{O}{\overset{\|}{C}}$—$\overset{H}{\overset{|}{N}}HR_5$ group wherein $R_5$ is hydrogen, a lower alkyl group of from 1 to 4 carbon atoms or a phenyl group.

Additionally, W may be an —$SO_3H$ or an —$COOR_3$ group wherein $R_3$ is hydrogen or a straight or branched alkyl group of from 1 to 4 carbon atoms, an alkanoyloxymethyl group in which the alkanoyl group is straight or branched and has from 2 to 5 carbon atoms, phenyl or indanyl.

Illustrative examples of alkyl groups as represented by $R_3$ are: methyl, ethyl, n-propyl, isopropyl, n-butyl and tert-butyl.

Illustrative examples of the alkanoyl groups as represented by $R_3$ are acetyl, propionyl and isobutyryl.

It is apparent that $R_1$ exhibits either a cis or a trans spatial relationship with the hydrogen at position 5 in compounds of Formula 1. The cis and trans isomers are within the scope of the invention; the compounds with the cis configuration being preferred.

The non-toxic pharmaceutically acceptable acid addition salts of compounds of Formula 1 such as mineral acids, for example, hydrogen chloride, hydrogen bromide, hydrogen iodide, sulfate, sulfonate and phosphate and organic acid addition salts, for example, maleate, acetate, citrate, oxalate, succinate, benzoate, tartrate, fumarate, malate, mandelate and ascorbate are also included within the scope of this invention.

Also within the scope of this invention are the nontoxic pharmaceutically acceptable salts of compounds of Formula 1 wherein W represents —$CO_2R_3$ or —$SO_3H$ ($R_3$=H) and $R_2$ is hydrogen. Illustrative examples of these salts are the acid derivatives of primary, secondary and tertiary amines such as cyclohexylamine, dibutylamine, trioctylamine, procaine and dibenzylamine and the alkali metal and alkaline earth metal cations such as sodium, potassium, magnesium and calcium.

The compounds of this invention may be administered in a manner similar to that of many well known penicillin derivatives such as penicillin G, N and V. They may be administered orally or parenterally to warm blooded animals, that is, birds and mammals, for example, cats, dogs, cows, sheep, horses and humans. For oral administration the compounds may be administered in the form of tablets, capsules or pills or in the form of elixirs or suspensions. For parenteral administration they may be used in the form of sterile aqueous solutions which may contain other solutes, for example, enough saline or glucose to make the solutions isotonic.

Illustrative examples of bacteria against which the compounds of this invention are active are *Staphylococcus aureus, Streptococcus pyregens* and *Diplococcus pneumoniae*.

The preferred compounds of this invention are those compounds of Formula 1 where X is methoxy and azido, $R_1$ is hydrogen, $R_2$ is hydrogen and W is hydrogen, hydroxyl, carboxyl, sulfo, amino, tert-butyloxycarbonylamino and ureido. The more preferred compounds are compounds of Formula 1 wherein X is methoxy and azido, $R_1$ and $R_2$ are both hydrogen and W is amino, tert-butyloxycarbonylamino and ureido.

An illustrative example of a compound of this invention is 6-[[(tert-butyloxycarbonyl)[4-hydroxy-3-(methoxymethyl)phenyl]acetyl]amino]-3,3-dimethyl-7-oxo-4-thia-1-azabicyclo[3.2.0]heptane-2-carboxylic acid.

Compounds of Formula 1 may be prepared by coupling compounds of Formula 2

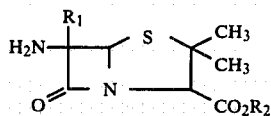

Formula 2 with compounds of Formula 3

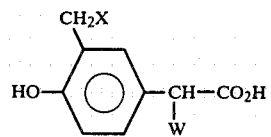

Formula 3 or functional equivalents thereof wherein $R_1$, $R_2$ and W are as defined for Formula 1, X is other than —$SO_3H$ and with a proviso that when X is chlorine or bromine, $R_4$ is other than tert-butyloxycarbonyl. It is provided that when W is an —$NHR_4$ ($R_4$ is hydrogen) or an —OH group, these groups must be protected during the coupling reaction. When W is a —$CO_2R_3$ or an —$SO_3H$ ($R_3$ is hydrogen), these groups may be protected. Optionally the coupling reaction may be run in the presence of a dehydrating agent such as a carbodiimide.

After the coupling reaction is completed, the protecting groups may be removed. For example, acid hydrolysis as illustrated in *Chem. Ber.*, 98, 789 (1965) or hydrogenolysis as illustrated in *J. Chem. Soc.*, 1440 (1962) may be used to remove the protecting groups from the amino or hydroxyl groups. Neutralization with base of the amine salts removes the protecting hydrohalide salts of amines.

Illustrative examples of protecting groups which are used for the specific reactive groups such as —$NHR_4$, —OH, —$CO_2R_3$ and —$SO_3H$ wherein $R_3$ and $R_4$ are H are as follows. For an amine group the protecting group may be an acid salt such as the amine hydrochloride, an alkoxycarbonyl group, for example, tert-butoxycarbonyl; an alkanoyl group, for example, an acetyl group, a [3-ethoxy-1-methyl-3-oxo-1-propen-1-yl] group or a benzyloxycarbonyl group. The hydroxyl group may be protected with a trimethylsilyl group. Acid groups such as —$CO_2H$ and —$SO_3H$ may be protected with an alkyl group such as methyl, ethyl, tert-butyl or with an alkanoyloxymethyl group such as pivaloyloxymethyl.

Functional equivalents of the acid as represented by compounds of Formula 3 include the acid halide such as the acid chloride, acid anhydrides, including mixed anhydrides, with for example, alkylphosphoric acids, lower aliphatic monoesters of carbonic acid or alkyl or aryl sulfonic acids.

The coupling reaction is generally carried out in the presence of a solvent. Suitable solvents include, for example, ethyl acetate, chloroform, acetone, dioxane, tetrahydrofuran THF, dimethylformamide (DMF), ether, ethanol, benzene and ethanol-benzene. As hydrophilic solvents are employed, mixtures of these solvents with water are also suitable for the above reactions. The coupling reaction is generally carried out in the presence of a base, for example, triethylamine or an alkanline bicarbonate. The temperature of the reaction may vary from $-10°$ C. to $100°$ C., and the reaction time may vary from about ½ hour to 10 hours. The penicillin products are isolated by conventional means.

Illustratively, an acid as represented by Formula 3 may be coupled to a compound as represented by Formula 2 using the general procedure described in J. Med. Chem., 9, 746 (1966) with the proviso that when W is other than hydrogen, these groups such as —$NHR_4$, —OH, —$CO_2R_3$ and —$SO_3H$ ($R_3$ and $R_4$ are hydrogen) may be protected. The acid to be coupled is reacted with an alkylchloroformate such as isobutylchloroformate at about $-10°$ C. in a solvent which contains an acid acceptor such as triethylamine or sodium bicarbonate. After reaction is complete, 1 equivalent of a compound represented by Formula 2 is added, the temperature is raised from $-10°$ C. to about $20°$ C. and the reaction completed after 2–3 hours. The coupled product is recovered by known means.

Illustratively, an acid, as represented by compounds of Formula 3 wherein W is H, —OH, —$NHR_4$, —$CO_2R_3$ and —$SO_3H$ ($R_3$ and $R_4$ are hydrogen) may be coupled to an amine as represented by a compound of Formula 2 in a suitable solvent by the use of a carbodiimide, for example, N,N'-dicyclohexylcarbodiimide by the general procedure as taught in U.S. Pat. No. 3,252,973, with the proviso that —OH, —$NHR_2$, —$CO_2H$ and —$SO_3H$ may be protected.

Illustratively, an acid as represented by compounds of Formula 3 may be converted to an acid chloride by means well known in the art. The active groups such as —$NHR_4$ and —OH must be protected whereas the groups —$CO_2R_3$ or —$SO_3H$, $R_3=R_4=H$, may be protected prior to formation of acid chloride when present as part of Formula 3. The acid chloride is reacted with an amine as represented by Formula 2 in a suitable solvent which generally contains an acid acceptor such as triethylamine or an alkaline bicarbonate to give a compound of Formula 1. The product is recovered by conventional methods.

Compounds of Formula 1 wherein $R_1$ and $R_2$ are as defined in Formula 1, X is other than $R_6SO$—, $R_6SO_2$, chlorine or bromine, W is as defined for Formula 1 with the proviso that $R_4$ is other than tert-butyloxycarbonyl may be prepared by reacting 1 equivalent of a compound of Formula 1 where X is chlorine or bromine and $R_4$ is other than tert-butyloxycarbonyl with from 1 to 10 equivalents of a nucleophilic reagent in a suitable solvent, for example, tetrahydrofuran, water, dimethylformamide, dimethylsulfoxide, acetone, chlorinated aliphatic hydrocarbons such as methylene chloride, chloroform or ethylene dichloride at a temperature of about $10°$ to $100°$ C. for from 0.5 hour to 48 hours. The nucleophilic reagent may be selected from sodium azide, silver cyanide, methanol, sodium methoxide, sodium methylthiolate, calcium cyanamide, sodium bisulfite, ammonium thiocyanate, silver cyanate, sodium methanesulfonamide, thiourea, thiosemicarbazide, guanylthiourea, ethylene thiourea, formylthiosemicarbazide, silver trifluoromethylthiolate, sodium thiosulfite, 2,3 or 4-mercaptopyridine, sodium sulfide, 1-methyltetrazol-5-ylthiol, 1,3,4-thiadiazol-5-ylthiol, 1,3,4-triazol-2-ylthio, potassium ethylxanthate,

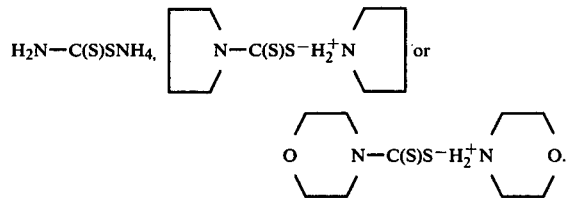

Compounds of Formula 3 are prepared by methods described herein.

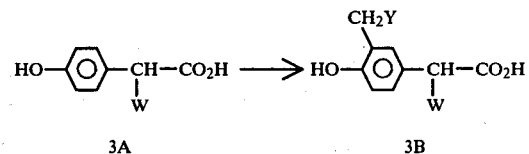

Compounds of Formula 3A wherein W is hydrogen, hydroxyl, amino and carboxyl optionally substituted with a 1 to 4 carbon alkyl group, a phenyl group or an indanyl group, sulfo or ureido which may optionally be mono-substituted with an alkyl group of from 1 to 4 carbon atoms or a phenyl group are commercially available, are described in the literature or are described herein, may be reacted with an equivalent amount of formaldehyde in a reaction medium such as hydrochloric acid, hydrobromic acid, acetic acid, phosphoric acid or sulfuric acid, optionally in the presence of a Lewis acid catalyst such as $AlCl_3$, $TiCl_4$ or $SnCl_4$ at $-10°$ C. to $100°$ C. for from 30 minutes to 10 hours. Gaseous hydrogen chloride or hydrogen bromide is passed through the reaction medium. A compound of Formula 3B wherein Y is chlorine or bromine is obtained.

Compounds of Formula 3 wherein X is other than $R_6SO_4$—, $R_6SO_2$, chlorine or bromine may be prepared by the nucleophilic displacement of a halogen atom from 1 equivalent of a compound of Formula 3B with from 1 to 10 equivalents of a nucleophile, MZ.

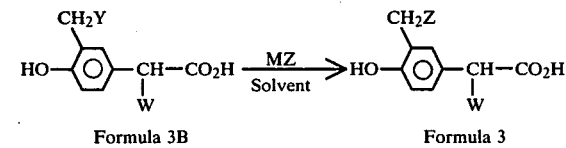

W is as defined for Formula 1 with the proviso that $R_4$ is other than tert-butyloxycarbonyl and Y is chlorine or bromine.

The nucleophiles, represented by MZ, are commercially available or may be prepared by standard procedures known in the art. Illustratively, compounds represented by MZ may be the following: sodium azide, silver cyanide, methanol, sodium methoxide, sodium methylthiolate, calcium cyanamide, sodium sulfite, potassium bisulfite, ammonium thiocyanate, silver cyanate, sodium methanesulfonamide, thiourea, thiosemicarbazide, guanylthiourea, ethylene thiourea, formylthiosemicarbazide, silver trifluoromethylthiolate, sodium thiosulfite, 2,3 or b 4-mercaptopyridine, sodium sulfide, 1-methyltetrazol-5ylthiol, 1,3,4-thiadiazol-5-ylthiol, 1,3,4-triazol-2-ylthio, potassium ethylxanthate, $H_2N-C(S)SNH_4$,

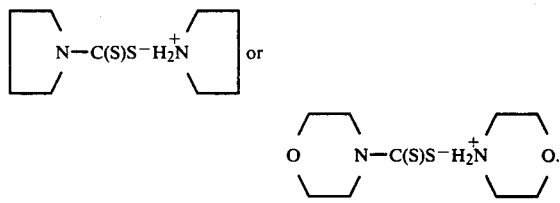

The nucleophilic displacement reaction is conducted in a suitable solvent such as water, methanol, ethanol, isopropanol, dimethylformamide, dimethylsulfoxide, acetonitrile, acetone and mixtures thereof at temperatures from 0° to 100° C. for from 0.5 hour to 48 hours.

Compounds of Formula 3 where X is an $R_6SO$— or an $R_6SO_2$— group may be prepared by the stepwise sulfur-oxidation of compounds of Formula 3 where X is an $R_6S$— group. For example, the stepwise sulfur-oxidation may be carried out in a suitable solvent such as water, water-methanol, or water-acetic acid with an equivalent or an excess of a sulfur-oxidizing agent at a temperature of 0° to 50° C. for from 3 to 15 hours. An equivalent amount of the sulfur-oxidizing agent gives the $R_6SO$—compound, an excess of the sulfur-oxidizing agent gives the $R_6SO_2$—compound.

Compounds of Formulas 1 and 3 where $R_4$ is a tert-butyloxycarbonyl group may be prepared from the corresponding compounds of Formulas 1 and 3 where $R_4$ is hydrogen and X is other than chlorine or bromine. For example, an equivalent of a compound of Formula 1 or 3 wherein $R_2$ is hydrogen may be reacted with 1 to 2 equivalents of a reagent such as tert-butyloxycarbonylazide, 2-(tert-butyloxycarbonyloxyimino)-2-phenylacetonitrile or di-tert-butyldicarbonate at a temperature of from 10° to 60° C. for from 2 hours to 20 hours in a suitable solvent, for example, water, dioxane, tert-butanol or mixtures thereof and in the presence of a basic material, for example, magnesium oxide, triethylamine or sodium hydroxide.

Compounds of Formula 2 wherein $R_1$ is hydrogen and $R_2$ is hydrogen are commercially available or may be prepared by methods well known in the art. Compounds of Formula 2 wherein $R_1$ is methoxy and $R_2$ is hydrogen are prepared according to the general procedures described in U.S. Pat. No. 3,778,432.

Compounds of Formulas 1 and 2 wherein $R_2$ is alkanoyloxymethyl may be prepared by reacting the corresponding acid, $R_2$ is hydrogen and $R_3$ is other than hydrogen, in the form of a salt, such as an alkali metal salt or the triethylammonium salt with an equivalent of a compound of the formula:

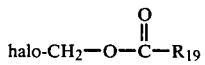

wherein halo is chloride or bromine, and $R_{19}$ is a straight or branched alkyl group of from 1 to 4 carbon atoms, by the general procedure described in U.S. Pat. No. 3,655,658.

Compounds of Formulas 1 and 2 wherein $R_2$ is alkanoylaminomethyl or alkoxycarbonylaminomethyl are prepared by treating the sodium salt of the corresponding acid, $R_2$ is hydrogen and $R_3$ is other than hydrogen, derivatives of Formulas 1 and 2 in an organic solvent such as dimethylformamide or hexamethylphosphoramide at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of Formulas 1 and 2 wherein $R_2$ is p-(alkanoyloxy)benzyl are prepared by adding 2 equivalents of the p-(alkanoyloxy)benzyl alcohol to an equivalent of the sodium salt of the corresponding acid derivative, $R_2$ is hydrogen and $R_3$ is other than hydrogen, of Formulas 1 and 2 and dimethylformamide or hexamethylphosphoramide after which the mixture is cooled to 0° C. One to 2 equivalents of dicyclohexylcarbodiimide and dimethylformamide are added dropwise to the mixture with stirring. The mixture is stirred at 0° C. for ½ to 3 hours and then an additional 2 to 5 hours at room temperature. The formed dicyclohexylurea is removed by filtration and the filtrate is diluted with chloroform, methylene chloride or ethyl acetate, washed with water and dried to give the product.

Compounds of Formulas 1 and 2 wherein $R_2$ is aminoalkanoyloxymethyl are prepared by mixing a suspension of the sodium salt of an acid of Formul 1 or 2 with an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethyl acetate or methylene chloride, washed with water, aqueous base and then water. The organic phase is separated and the precipitate isolated by conventional means followed by deprotection of the amine group to give the product.

The acids as represented by compounds of Formula 3 are coupled as the (+)-, the (−)- or mixtures of the (+) and (−) optical isomers when W is other than hydrogen or—$CO_2R_5$. When W is hydrogen or—$CO_2R_5$, no optical activity is present and these compounds are coupled as described above.

The daily dosage of the active ingredient may range from 1 mg to about 500 mg. The exact amount will vary with the patient's size, age and type of infection.

A typical tablet can have the following composition:

| | |
|---|---|
| 6-[[amino[4-hydroxy-3-(methoxymethyl)-phenyl]acetyl]amino]-3,3-dimethyl-7-oxo-4-thia-1-azabicyclo[3.2.0]heptane-2-carboxylic acid | 125 mg |
| Lactose, USP | 250 mg |
| Cornstarch, USP | 50 mg |
| Cornstarch, USP (as 10% starch paste) | 5 mg |
| Calcium Stearate | 2 mg |

The penicillin derivative, lactose and cornstarch are mixed and ground through a number 12 screen. The ground material is mixed with additional cornstarch as 10% starch paste and calcium stearate. Suitable size tablets can be prepared using a 5/16 inch diameter standard concave punch.

A typical parenteral solution may have the following composition:

| | |
|---|---|
| 6-[[amino[4-hydroxy-3-(methoxymethyl)-phenyl]acetyl]amino]-3,3-dimrthyl-7-oxo-4-thia-1-azabicyclo[3.2.0]heptane-2-carboxylic acid | 0.250 g |
| Sodium citrate | 0.006 g |
| Polyvinylpyrrolidone | 0.003 g |
| Lecithin | 0.010 g |
| Sodium carboxymethylcellulose | 0.003 g |
| Preservatives | |
| Methylparaben | 0.09% |
| Propylparaben | 0.01% |
| Sterile water to make | 1 cc |

Quantities required to make 1000 cc of parenteral solution, less the penicillin compound, are dissolved in about 250 cc of sterile water. The penicillin compound is added along with 100 cc of sterile water. The mixture is stirred and the final volume brought to 1000 cc by the addition of sterile water.

EXAMPLE 1

(−)-α-Amino-3-(chloromethyl)-4-hydroxybenzeneacetic acid hydrochloride

To a solution of (−)-α-amino-4-hydroxybenzeneacetic acid (100 g, 0.6 mole) in a minimum amount of concentrated hydrochloric acid at 35°–40° C. is added 50 ml of aqueous formaldehyde (35–37%) (0.6 mole). The addition of hydrogen chloride gas is begun. After 5–10 minutes, a solid begins to precipitate. Stirring is continued for 30 minutes, and the solid is then collected. The crude product is washed with ether and with acetone. A second crop is obtained from the filtrate after standing at room temperature overnight. Total yield is 102 g (67%) m.p.>300° C., $[\alpha]_D^{18} = -134°$ (c 4.75, $CH_3OH$) MNR ($DMSO-D_6$) ppm (δ) 4.68 (s,2), 4.9 (broad s,1), 6.9–7.6 (superimposed q and s,3).

Anal. calcd for $C_9H_{10}ClNO_3 \cdot HCl$: Cl 28.13. Found 26.44

In like manner and using equivalent amounts of (−)-α-amino(4-hydroxybenzene)acetic acid, ethyl ester hydrochloride in place of (−)-α-amino(4-hydroxybenzene)acetic acid gives (−)-α-amino-3-chloromethyl-4-hydroxybenzeneacetic acid, ethyl ester, hydrochloride.

EXAMPLE 2

(−)-α-Amino-3-(bromomethyl)-4-hydroxybenzeneacetic acid hydrobromide

To a solution of (−)-α-amino-4-hydroxybenzeneacetic acid (0.6 mole) in a minimum amount of concentrated hydrobromic acid at 35°–40° C. is added 50 ml of aqueous formaldehyde (35–37%) (0.6 mole). The addition of hydrogen bromide gas is begun. After 5–10 minutes, a solid begins to precipitate. Stirring is continued for 30 minutes. The title compound is collected and washed with ether and acetone.

EXAMPLE 3

3-Chloromethyl-4-hydroxybenzeneacetic acid

4-Hydroxybenzene acetic acid, 0.5 mole, is added to concentrated hydrochloric acid, 50 ml, then 0.5 mole of formaldehyde in the form of a 34–38% solution of formalin is added. Hydrogen chloride is bubbled through the reaction mixture for 60 minutes while maintaining the temperature of the reaction mixture at 35° to 45° C. The reaction mixture is poured into water and the title compound is extracted from the aqueous solution with ethyl acetate. The ethyl acetate is dried over magnesium sulfate, filtered and removed to give the title compound.

EXAMPLE 4

α-Hydroxy-3-(bromomethyl)-4-hydroxybenzeneacetic acid

About 0.3 mole of a α-hydroxy(4-hydroxybenzene)acetic acid is added to about 50 ml of concentrated hydrobromic acid containing about 0.1 mole trioxane. The temperature is maintained between about 35° to about 45° C. while passing hydrogen bromide gas through the reaction mixture. After about 90 minutes, the reaction mixture is poured into cold water and the title compound is extracted with ethyl acetate. After drying the organic extract over magnesium sulfate and filtering to remove the magnesium sulfate, removal of the ethyl acetate gives the title compound.

EXAMPLE 5

α-Carboxy-3-(bromomethyl)-4-hydroxybenzeneacetic acid

About 0.5 mole of 4-hydroxybenzeneacetic acid is dissolved in about 50 ml of anhydrous tetrahydrofuran at −40° C. To this solution is added 3 equivalents of lithium diisopropylamide. The temperature is maintained at about −40° C. for about 15 minutes. Then 1 equivalent of ethyl chloroformate is added and the temperature is raised from about −40° C. to about 20° C. and the reaction mixture stirred for about 60 minutes. The reaction mixture is poured into water and the monoester of α-carboxy-4-hydroxybenzeneacetic acid is recovered from the aqueous solution. Hydrolysis of the half-ester with sodium hydroxide followed by acidification with hydrochloric acid gives α-carboxy-4-hydroxybenzeneacetic acid.

α-Carboxy-4-hydroxybenzeneacetic acid, 0.3 mole, is added to aqueous acetic acid (50%) which contains 0.3 mole of chloromethyl methyl ether and a catalytic amount of zinc chloride. The temperature is maintained between about 35° to 45° C. for about 2 hours while hydrogen chloride gas is bubbled through the solution. The reaction mixture is then added to water and the reaction product is recovered by extraction with methylene chloride. After drying the methylene chloride over magnesium sulfate, the magnesium sulfate is removed by filtration. Removal of the methylene chloride gives the title compound.

EXAMPLE 6

α-Sulfo-3-(chloromethyl)-4-hydroxybenzeneacetic acid

Approximately 0.6 mole of 4-hydroxybenzeneacetic acid is added to about 0.9 mole of dioxane-$SO_3$ complex in ethylene chloride maintained at room temperature. This mixture is then stirred at room temperature for 16 hours. The reaction mixture is poured into water and the α-sulfo-(4-hydroxybenzene)acetic acid is recovered from the aqueous solution by evaporation of the dioxane and ethylene chloride.

α-Sulfo-4-hydroxybenzeneacetic acid, 0.3 mole, is dissolved in aqueous sulfuric acid (50%). One equivalent of dichloromethyl ether is added to the solution maintained at between 35° to 45° C. Hydrogen chloride is then bubbled through this reaction mixture for 3 hours. The desired compound is recovered by pouring the reaction mixture into water and extracting the title compound with ethyl acetate. The ethyl acetate is dried over magnesium sulfate. The magnesium sulfate is removed by filtration and evaporation of the ethyl acetate gives the desired compound.

EXAMPLE 7

α-(Aminocarbonyl)amino-3-(chloromethyl)-4-hydroxybenzeneacetic acid

To about 0.15 mole of α-amino-4-hydroxybenzeneacetic acid dissolved in 700 ml of water and 0.2 mole of glacial acetic acid is added about 0.2 mole of potassium cyanate. The resulting mixture is stirred at room temperature for about 30 minutes. The reaction mixture is saturated with sodium chloride and then extracted with ethyl acetate. The ethyl acetate is washed with water, dried over magnesium sulfate, filtered and evaporated to give α-(aminocarbonyl)amino-4-hydroxybenzeneacetic acid.

Equivalent amounts (0.1 mole) of α-(aminocarbonyl)-amino-4-hydroxybenzeneacetic acid and formaldehyde as a 34–38% formalin solution are added to 250 ml of concentrated hydrochloric acid. The temperature is maintained between 20° to 40° C. and gaseous hydrogen chloride is added over a period of 2 hours. The solution thus obtained is concentrated under vacuum and the residue is extracted with ethyl acetate. The ethyl acetate extract is washed with water, dried over magnesium sulfate and evaporated to give the title compound.

EXAMPLE 8

(−)-α-Amino-3-(azidomethyl)-4-hydroxybenzeneacetic acid

To a solution of (−)-α-amino-3-(chloromethyl)-4-hydroxybenzeneacetic acid (252 mg, 1 mmole) in 4 ml of methyl alcohol is added sodium azide (156 mg, 2.4 mmole). The mixture is stirred at about 40° C. for 15 minutes. After about 10 minutes the title compound begins to precipitate. The mixture is cooled, filtered and the product is washed with a small amount of methyl alcohol and acetone. The title compound is collected (210 mg, 95% yield). M.P. >300°; $[\alpha]_D^{18} = -73.03°$ (c 1.7, water), NMR (DMSO-$D_6$) ppm (δ) 4.22 (s,1), 4.35 (s,2), 6.7–7.5 (superimposed q and s,3).

Anal. calcd for $C_9H_{10}N_4O_3$: N 25.21; Found N, 23.83.

EXAMPLE 9

(−)-α-Amino-3-(thiocyanatomethyl)-4-hydroxybenzeneacetic acid

A solution of (−)-α-amino-3-(chloromethyl)-4-hydroxybenzeneacetic acid (0.5 g, 1.98 mmole) and potassium thiocyanate (0.4 g, 4.12 mmole) in 10 ml of methanol is stirred at room temperature for 16 hours. The reaction mixture is filtered to remove the potassium chloride, the filtrate is evaporated and to the residue is added saturated aqueous sodium bicarbonate until the pH is 7. The title compound precipitates as a white powder which is filtered and dried. (1.83 g, 78% yield), NMR TFA-D+D+$D_2O$) ppm (δ) 4.1 (s,2), 5.08 (s,1), 6.9–7.3 (m,3).

EXAMPLE 10

(−)-α-Amino-4-hydroxy-3-(methoxymethyl)benzeneacetic acid methyl ester hydrochloride A solution of (−)-α-amino-3-(chloromethyl)-4-hydroxybenzeneacetic acid (1 g, 3.96 mmole) in 10 ml of methanol is refluxed for 30 hours. The solvent is then removed under vacuum and the title compound is isolated in quantitative yield as a hygroscopic powder.

NMR (DMSO-$D_6$+$D_2O$) ppm (δ) 3.40 (s,3), 3.78 (s,3), 4.47 (s,2), 5.20 (s,1), 7.0–7.7 (m,3).

EXAMPLE 11

(−)-α-Amino-4-hydroxy-3-(methoxymethyl)benzeneacetic acid methyl ester (−)-α-Amino-4-hydroxy-3-(methoxymethyl)benzeneacetic acid methyl ester hydrochloride is dissolved in a minimum amount of methanol. To this solution is added methanolic potassium hydroxide until a basic reaction to phenolphthalein is observed. The potassium chloride which precipitates is removed and the solvent is removed under vacuum to give a quantitative yield of the title compound.

NMR (DMSO-$D_6$+$D_2O$) ppm (δ) 3.32 (s,3), 3.64 (s,3), 4.4 (superimposed s,2 and s,1), 6.6–7.3 (m,3).

EXAMPLE 12

(−)-α-Amino-4-hydroxy-3-(methoxymethyl)benzeneacetic acid (−)-α-Amino-4-hydroxy-3-(methoxymethyl)benzeneacetic acid methyl ester is dissolved in aqueous 1 N sodium hydroxide and the solution is stirred at 40°–50° C. for 1 hour. The solution is acidified with 6 N hydrochloric acid to a pH of 7. Evaporation of the solvent gives the title compound in a 90% overall yield.

NMR ($D_2O$) ppm (δ) 3.42 (s,3), 4.56 (s,2), 5.2 (s,1), 7.0–7.5 (m,3).

EXAMPLE 13

(−)-α-Amino-3-[[(aminoiminomethyl)thio]methyl]-4-hydroxybenzeneacetic acid dihydrochloride A solution of (−)-α-amino-3-(chloromethyl)-4-hydroxybenzeneacetic acid (2 g, 8 mmole) and thiourea (0.61 g, 8 mmole) in 10 ml of water is stirred at room temperature for 4 hours. Removal of the solvent by lyophilization gives a quantitative yield of the title compound, isolated as its dihydrochloride, $[\alpha]_D^{25} = -69.2°$ (c, 10.4, $H_2O$), NMR (TFA-D) 4.34 (s,2), 5.4 (s,1), 6.8–7.6 (m,3).

EXAMPLE 14

(−)-α-Amino-3-[[(4,5-dihydro-1H-imidazol-2-yl)thio]methyl]-4-hydroxybenzeneacetic acid dihydrochloride The title compound as its dihydrochloride is obtained as described in Example 13 when thiourea is replaced by 2-imidazolidinethione. $[\alpha]_D^{25} = -53.41°$ (c, 9.4, $H_2O$), NMR (TFA-D+$D_2O$) ppm (δ) 4.05 (s,4), 4.41 (s,2), 5.16 (s,1), 6.9–7.7 (m,3).

EXAMPLE 15

(−)-α-Amino-4-hydroxy-3-[[(2-methyl-1H-tetrazol-5-yl)thio]-methyl]benzeneacetic acid hydrochloride The title compound as its hydrochloride is obtained by the procedure described in Example 13 when thiourea is replaced by 1-methyl-1H-tetrazol-5-ylthiol. $[\alpha]_D^{25} = -47.8°$ (c 11.86, $H_2O$), NMR (TFA-D+$D_2O$) 3.96 (s,3), 4.42 (s,2), 5.17 (s,1), 6.8–7.6 (m,3).

EXAMPLE 16

(−)-α-Amino-4-hydroxy-3-(sulfomethyl)benzeneacetic acid monosodium salt

The title compound is obtained after an aqueous solution of sodium sulfite (4 mmole) and (−)-α-amino-3-(chloromethyl)-4-hydroxybenzeneacetic acid (1 g, 4 mmole) in 15 ml of water is refluxed for 3 hours. Lyophilization of the solvent gives the title compound as its sodium salt.

NMR (TFA−D+D$_2$O) ppm (δ) 4.1 (s,2), 5.0 (s,1), 6.7−7.4 (m,3).

EXAMPLE 17

(−)-α-Amino-3-[[[[(aminoiminomethyl)amino]iminomethyl]-thio]methyl]-4-hydroxybenzeneacetic acid dihydrochloride A solution of (−)-α-amino-3-(chloromethyl)-4-hydroxybenzeneacetic acid (1 g, 0.4 mmole) and N-(aminoiminomethyl)thiourea (0.47 g, 4 mmole), in 10 ml of water is stirred at room temperature for 4.5 hours. Removal of the solvent by lyophilization gives a quantitative yield of of the title compound, isolated as its dihydrochloride.

NMR (TFA−D+D$_2$O) ppm (δ) 4.2 (s,2), 5.2 (s,1), 6.8−7.3 (m,3).

EXAMPLE 18

(−)-α-Amino-4-hydroxy-3-(hydroxymethyl)benzeneacetic acid

To a solution of (−)-α-amino-3-(chloromethyl)-4-hydroxybenzeneacetic acid hydrochloride in water is added saturated aqueous sodium bicarbonate until a pH of 7 is reached. The solution is stirred overnight and is then lyophilized to give a quantitative yield of the title compound, combined with 2 equivalents of sodium chloride.

NMR (TFA−D+D$_2$O) ppm (δ) 4.73 (s,2), 5.1 (s,1); 6.9−7.3 (m,3).

EXAMPLE 19

(−)-α-Amino-4-hydroxy-3-[(methylthio)methyl]benzeneacetic acid

To a solution of methanethiol (3 g, 0.04 mmole) in 250 ml of water is added sodium hydroxide (0.04 mole) followed by (−)-α-amino-3-(chloromethyl)-4-hydroxybenzeneacetic acid hydrochloride (5 g, 0.02 mole). The solution obtained is stirred overnight. Removal of the solvent by flash evaporation gives a quantitative yield of the title compound combined with 2 equivalents of sodium chloride.

NMR (TFA−D+D$_2$O) ppm (δ) 2.14 (s,3), 3.78 (s,2), 5.18 (s,1), 6.9−7.3 (m,3).

EXAMPLE 20

(−)-α-Amino-3-[[(ethoxythioxomethyl)thio]methyl]-4-hydroxybenzeneacetic acid

To a solution of (−)-α-amino-3-(chloromethyl)-4-hydroxybenzeneacetic acid hydrochloride (1 g, 0.004 mole) in 20 ml of water is added carbonodithioic acid, O-ethyl ester, potassium salt (1.26 g, 0.08 mole). Within a few minutes a precipitate begins to form. The mixture is stirred at room temperature for 3 hours. The solid precipitate is filtered, washed with water and dried to give 58.3% of the title compound.

[α]$_D^{25}$ = −81.1° (CH$_3$OH, c 5.82), NMR (TFA−D+D$_2$O) ppm (δ) 1.4 (t,3), 4.37 (s,2), 4.6 (q,2), 5.03 (s,2), 6.7−7.5 (m,3).

EXAMPLE 21

3-Azidomethyl-4-hydroxybenzeneacetic acid

A solution of 3-chloromethyl-4-hydroxybenzeneacetic acid (0.1 mole) and sodium azide (0.1 mole) in 250 ml of water is stirred at room temperature for about 16 hours. Removal of the solvent gives the title compound combined with sodium chloride.

Using the procedure described above, the following products are obtained from the thus listed starting materials.

| STARTING MATERIALS | | |
|---|---|---|
| SUBSTITUTED BENZENEACETIC ACIDS | NUCLEOPHILE | PRODUCT |
| α-Hydroxy-3-(chloromethyl)-4-hydroxybenzeneacetic acid | Thiourea | α-Hydroxy-3-[[(aminoiminomethyl)thio]methyl]-4-hydroxybenzeneacetic acid |
| α-Carboxy-3-bromomethyl-4-hydroxybenzeneacetic acid | Potassium methylthiolate | α-Carboxy-4-hydroxy-3-[(methylthio)methyl]benzeneacetic acid |
| α-Sulfo-3-chloromethyl-4-hydroxybenzeneacetic acid | Ammonium cyanate | α-Sulfo-3-(cyanatomethyl)-4-hydroxybenzeneacetic acid |
| α-(Aminocarbonyl)amino-3-chloromethyl-4-hydroxybenzeneacetic acid | Sodium cyanide | α-(Aminocarbonyl)amino-3-(cyanomethyl)-4-hydroxybenzeneacetic acid |
| α-Amino-3-(chloromethyl)-4-hydroxybenzeneacetic acid | Calcium cyanamide | α-Amino-3-(cyanoamino)methyl]-4-hydroxybenzeneacetic acid |
| α-Amino-3-(chloromethyl)-4-hydroxybenzeneacetic acid | Thiosemicarbazide | α-Amino-3-[[(aminohydrazonomethyl)thio]methyl]-4-hydroxybenzeneacetic acid |
| α-Amino-3-(chloromethyl)-4-hydroxybenzeneacetic acid | Formylthiosemicarbazide | α-Amino-3-[[[amino(formylhydrazono)methyl]thio]methyl]-4-hydroxybenzeneacetic acid |
| α-Amino-3-(chloromethyl)-4-hydroxybenzeneacetic acid | 2-Pyridinethiol | α-Amino-4-hydroxy-3-[(2-pyridinylthio)methyl]benzeneacetic acid |
| α-Amino-3-(chloromethyl)-4-hydroxybenzeneacetic acid | 1,3,4-thiadiazol-2-ylthiol | α-Amino-4-hydroxy-3-[(1,3,4-thiadiazol-2-ylthio)methyl]benzeneacetic acid |
| α-Amino-3-(chloromethyl)-4-hydroxybenzenecetic acid | 1-H-1,2,4-triazol-3-ylthiol | α-Amino-4-hydroxy-3-[(1H-1,2,4-triazol-3-ylthio)methyl]benzeneacetic acid |
| α-Amino-3-(chloromethyl)-4- | Na$_2$S | α-Amino-4-hydroxy-3-(mercapto- |

| STARTING MATERIALS | | |
|---|---|---|
| SUBSTITUTED BENZENEACETIC ACIDS | NUCLEOPHILE | PRODUCT |
| hydroxybenzeneacetic acid | | methyl)benzeneacetic acid |
| α-Amino-3-(chloromethyl)-4-hydroxybenzeneacetic acid | $NH_2CS_2NH_4$ | α-Amino-3-[[(aminothioxomethyl)-thio]methyl]-4-hydroxybenzeneacetic acid |

EXAMPLE 22

α-(Aminocarbonyl)amino-4-hydroxy-3-methylbenzeneacetic acid

A mixture of α-(aminocarbonyl)amino-3-chloromethyl-4-hydroxybenzeneacetic acid (0.1 mole) and 10% Pd on charcoal (1 g) catalyst in 50 ml of water is subjected to hydrogen gas at a pressure of about 60 pounds/in$^2$ at room temperature for a period of about 16 hours. Removal of the catalyst followed by evaporation of the water gives the title compound.

EXAMPLE 23

The following three procedures may be used to prepare compounds of Formula 1 wherein $R_4$ is tert-butyloxycarbonyl from the corresponding compounds wherein $R_4$ is hydrogen.

PROCEDURE I

To a mixture of an amino acid (40 mmole) and magnesium oxide (80 mmole) in 100 ml of 50% dioxane-water is added t-butyloxycarbonylazide (80 mmole). The mixture is stirred for 16–20 hours at 45°–50° C., it is then cooled, diluted with 400 ml of water and is extracted three times with ethyl acetate. The organic phase is subsequently washed with two portions of 20 ml of 1 N sodium bicarbonate and twice with water. The combined aqueous layers are cooled to 5° C. and acidified to pH 5 with cold 10% aqueous citric acid. The solution obtained is saturated with sodium chloride and is extracted with three portions of 400 ml of ethyl acetate. The organic phase is then dried over sodium sulfate, and the solvent is removed under vacuum. The desired N-tert-butyloxycarbonyl amino acid is thus isolated as an oil or a solid foam.

PROCEDURE II

To a solution of an amino acid (10 mmole) and triethylamine (15 mmole) in 12 ml of 50% water-dioxane is added 2-(tert-butyloxycarbonyloxyimino)-2-phenylacetonitrile (BOC-ON) (11 mmole). The mixture is stirred at room temperature for three hours. To the homogeneous mixture thus obtained, water (15 ml) and ethyl acetate (20 ml) are added. The aqueous phase is separated, washed with ethyl acetate (20 ml), acidified with 5% aqueous citric acid solution and extracted with ethyl acetate. The organic phase is dried and the solvent is removed under vacuum to give the N-tert-butyloxycarbonyl amino acid as an oil or a solid foam.

PROCEDURE III

To a well stirred solution of an amino acid (0.5 mole) and sodium hydroxide (0.5 mole) in 50 ml of water and 100 ml of tert-butanol is added di-tert-butyl dicarbonate [$(BOC)_2O$] (0.55 mole). The mixture is stirred overnight. The turbid solution obtained is diluted with water (250 ml) and is extracted with three portions of pentane (300 ml each). The aqueous phase is cooled, acidified to pH 2–3 with potassium hydrogen sulfate, and is extracted with four 400 ml portions of ethyl acetate. The combined organic phase is dried over anhydrous sodium sulfate, filtered and the solvent removed under reduced pressure. The desired N-tert-butyloxycarbonyl amino acid is thus obtained as an oil or a solid foam.

EXAMPLE 24

(−)-3-(Azidomethyl)-(tert-butyloxycarbonylamino)-4-hydroxybenzeneacetic acid

The title compound is obtained in 55% yield by Procedure I, Example 23, from (−)-α-amino-3-azidomethyl-4-hydroxybenzeneacetic acid.

NMR (CDCl$_3$) ppm (δ) 1.21 (s,9), 1.44 (s,2), 5.05 (broad s,1), 6.5–7.2 (m,3).

EXAMPLE 25

(−)-α-(tert-Butyloxycarbonylamino)-4-hydroxy-3-(methoxymethyl)benzeneacetic acid The title compound is obtained in 72% yield by Procedure I or in 83% yield by Procedure II, Example 23, from (−)-α-amino-4-hydroxy-3-(methoxymethyl)benzeneacetic acid.

NMR (CDCl$_3$) ppm (δ) 1.35 (s,9), 3.40 (s,3), 4.60 (s,2), 5.2 (broad s,1), 6.6–7.5 (m,3).

EXAMPLE 26

α-(tert-Butyloxycarbonylamino)[4-hydroxy-3-[(1-methyl-1H-tetrazol-5yl)thio]methyl]benzeneacetic acid The title compound is obtained in 30% yield by Procedure III, Example 23, from (−)-α-amino-4-hydroxy-3-[[(1-methyl-1H-tetrazol-5-yl)thio]methyl]benzeneacetic acid.

NMR (CDCl$_3$) ppm (δ) 1.37 (s,9), 3.7 (s,2), 3.8 (s,3), 5.15 (broad s,1), 6.8–7.4 (m,3).

EXAMPLE 27

(−)-(tert-Butyloxycarbonylamino)-3-(hydroxymethyl)-4-hydroxybenzeneacetic acid

The title compound is obtained in 76% yield by Procedure II, Example 23, from (−)-α-amino-4-hydroxy-3-(hydroxymethyl)benzeneacetic acid.

NMR (DMSO−D$_6$+D$_2$O) ppm (δ) 1.4 (s,9), 4.62 (s,2), 5.1 (s,1), 6.8–7.6 (m,3).

EXAMPLE 28

(−)-α-(tert-Butyloxycarbonylamino)-4-hydroxy-3-[(methylthio)methyl]benzeneacetic acid The title compound is obtained in 81% yield by Procedure III, Example 23, from (−)-α-amino-4-hydroxy-3-[(methylthio)methyl]benzeneacetic acid.

NMR (CDCl$_3$) ppm (δ) 1.4 (s,9), 1.97 (s,3), 3.68 (s,2), 5.1 (broad s,1), 6.6–7.5 (m,3).

EXAMPLE 29

(−)-α-tert-Butyloxycarbonylamino-3-[[(ethoxythiox-omethyl)thio[methyl[-4-hydroxybenzeneacetic acid The title compound is obtained in 91.5% yield when prepared according to Procedure III, Example 23, from (−)-α-amino-3-[[(ethoxythioxomethyl)thio]methyl]-4-hydroxybenzeneacetic acid.

NMR (CDCl$_3$) ppm (δ) 1.3–1.5 (superimposed t,3 and s,9), 4.21 (s,2), 4.5 (q,2), 4.96 (broad s,1), 6.4–7.2 (m,3).

EXAMPLE 30

(−)-α-Amino-4-hydroxy-3-[(methylsulfinyl)methyl]-benzeneacetic acid

To an aqueous solution (500 ml) of α-amino-4-hydroxy-3-[(methylthio)methyl]benzeneacetic acid (1 mole) is added sodium metaperiodate (1 mole). The mixture is stirred at room temperature for 5 hours, it is filtered and the filtrate is lyophilized to give a quantitative yield of the title compound.

NMR (DMSO−D$_6$+D$_2$O) ppm (δ) 2.65 (s,3), 4.12 (s,2), 4.5 (s,1), 6.8–7.5 (m,3).

EXAMPLE 31

(−)-α-Amino-4-hydroxy-3-[(methylsulfonyl)methyl]-benzeneacetic acid

A solution of α-amino-4-hydroxy-3-[(methylthio)methyl]-benzeneacetic acid (3 g, 8.7 mmole) and 30 ml of 30% hydrogen peroxide in 300 ml of acetic acid is stirred at room temperature for 17 hours. The mixture is filtered and the filtrate is flash concentrated at 35° C. It is mixed with methanol to give a solid which is washed with ether, filtered and dried to give the title compound in 92% yield $[\alpha]_D^{25} = -82.07°$ (dilute HCl, C 9.48).

NMR (TFA−D+D$_2$O) 2.75 (s,3), 4.17 (s,2), 4.8 (s,1), 6.5–7.3 (m,3).

EXAMPLE 32

(−)-α-tert-Butoxycarbonylamino-4-hydroxy-3-[(methylsulfinyl)methyl]benzeneacetic acid The title compound is obtained in 31% yield when prepared from (−)-α-amino-4-hydroxy-3-[(methylsulfinyl)methyl]benzeneacetic acid according to Procedure III in Example 23.

NMR (DMSO-D$_6$) ppm (δ) 1.4 (s,9), 5.47 (s,3), 4.0 (s,2), 4.98 (m,1), 6.5–7.5 (m,3).

EXAMPLE 33

(−)-α-tert-Butyloxycarbonylamino-4-hydroxy-3-[(methylsulfonyl)methyl]benzeneacetic acid The title compound is obtained in 36% yield when prepared according to Procedure III as described in Example 23 from (−)-α-amino-4-hydroxy-3-[(methylsulfonyl)methyl]benzeneacetic acid.

NMR (CDCl$_3$) ppm (δ) 1.36 (s,9), 2.67 (s,3), 4.3 (s,2), 5.15 (broad s,1), 6.5–7.4 (m,3).

EXAMPLE 34

α-(3-Ethoxy-1-methyl-3-oxo-1-propen-1-yl)amino-3-(azidomethyl)-4-hydroxybenzeneacetic acid α-Amino-3-(azidomethyl)-4-hydroxybenzeneacetic acid (20 mmole) is dissolved in 50 ml of 0.71 N methanolic potassium hydroxide. To this is added 21 mmole of ethyl acetoacetate in 10 ml of methanol. The resulting solution is heated to reflux for 15 minutes and cooled to about 10° C. to aid in the precipitation of the title compound which is recovered by filtration.

In like manner and using the appropriate quantities of the reagents, substitution of α-amino-4-hydroxy-3-(methoxymethyl)benzeneacetic acid; α-amino-4-hydroxy-3-[(methylthio)methyl]benzeneacetic acid; and α-amino-4-hydroxy-3-[(methylsulfonyl)methyl]benzeneacetic acid for α-amino-3-(azidomethyl)-4-hydroxybenzeneacetic acid gives the following compounds respectively:

α-(3-ethoxy-1-methyl-3-oxo-1-propen-1-yl)amino-4-hydroxy-3-(methoxymethyl)benzeneacetic acid;

α-(3-ethoxy-1-methyl-3-oxo-1-propen-1-yl)amino-4-hydroxy-3-[(methylthio)methyl]benzeneacetic acid; and α-(3-ethoxy-1-methyl-3-oxo-1-propen-1-yl)amino-4-hydroxy-3-[(methylsulfonyl)methyl]benzeneacetic acid.

EXAMPLE 35

6-[[Amino[4-hydroxy-3-(methoxymethyl)phenyl]acetyl]amino]-3,3-dimethyl-7-oxo-4-thia-1-azabicyclo[3.2.0]heptane-2-carboxylic acid α-(3-Ethoxy-1-methyl-3-oxo-1-propen-1-yl)amino-3-(azidomethyl)-4-hydroxybenzeneacetic acid (0.05 mole) is added to tetrahydrofuran (THF) at −10° C. Ethylchloroformate (0.05 mole) is slowly added with stirring while maintaining the temperature at −10° C. After 30 minutes, 6-amino-3,3-dimethyl-7-oxo-4-thia-1-azabicyclo[3.2.0]-heptane-2-carboxylic acid in 1 to 1 mixture of THF/water containing 0.05 mole of triethylamine is added to the thus formed solution. The mixture is stirred at −10° C. for about 30 minutes and then at about 20° C. for 30 minutes. The pH is adjusted to 2 and the reaction mixture is extracted with ethyl ether. The pH is then adjusted to 4.5 to 5.5 and the reaction mixture is extracted with ethyl acetate. The ethyl acetate is dried over sodium sulfate, filtered to remove the drying agent and evaporated to give the title compound.

In like manner and using the appropriate quantities of reagents, substitution of α-(3-ethoxy-1-methyl-3-oxo-1-propen-1-yl)amino-3-[[(aminoiminomethyl)thio]methyl]-4-hydroxybenzeneacetic acid; α-(3-ethoxy-1-methyl-3-oxo-1-propen-1-yl)amino-3-[[(4,5-dihydro-1H-imidazol-2-yl)-thio]methyl]-4-hydroxybenzeneacetic acid; or α-(3-ethoxy-1-methyl-3-oxo-1-propen-1-yl)amino-4-hydroxy-3-[(methylthio)methyl]benzeneacetic acid in place of α-(3-ethoxy-1-methyl-3-oxo-1-propen-1-yl)amino-3-(azidomethyl)-4-hydroxybenzeneacetic acid gives the following respective compounds: 6-[[Amino[3-[[(aminoiminomethyl)thio]methyl]-4-hydroxyphenyl]acetyl]amino]3,3-dimethyl-7-oxo-4-thia-1-azabicyclo[3.2.0]heptane-2-carboxylic acid; 6-[[amino-3-[[[(4,5-dihydro-1H-imidazol-2-yl)thio]methyl]-4-hydroxyphenyl]acetyl]amino]-3,3-dimethyl-7-oxo-4-thia-1-azabicyclo[3.2.0]heptane-2-carboxylic acid; and 6-[[amino[4-hydroxy-3-[(methylthio)methyl]phenyl]acetyl]-amino]-3,3-dimethyl-7-oxo-5-thia-1-azabicyclo[3.2.0]heptane-2-carboxylic acid.

EXAMPLE 36

α-(Benzyloxycarbonyl)amino-4-hydroxy-3-(methoxymethyl)-benzeneacetic acid

α-Amino-4-hydroxy-3-(methoxymethyl)benzeneacetic acid (0.1 mole), is dissolved in water, the pH of which is about 8. This solution is cooled to 0° C. and benzyl chloroformate (0.1 mole) is added dropwise along with 1N sodium hydroxide so as to maintain the pH at 8 to 9. After the addition, the solution is stirred at 0° C. for 30 minutes and 30 minutes at room temperature. The solution is washed with ethyl ether and then acidified with hydrochloric acid. The title compound is then recovered from the aqueous solution.

EXAMPLE 37

6-[[Amino[4-hydroxy-3-(methoxymethyl)phenyl]acetyl]amino]-3,3-dimethyl-7-oxo-4-thia-1-azabicyclo[3.2.0]heptane-2-carboxylic acid α-(Benzyloxycarbonyl)amino-4-hydroxy-3-(methoxymethyl)benzeneacetic acid (0.1 mole) is dissolved in tetrahydrofuran (THF). The temperature of the solution is maintained at about −10° C. and 0.2 mole of isobutylchloroformate is added. After stirring for about 30 minutes at −10° C., 0.1 mole of 6-amino-3,3-dimethyl-7-oxo-4-thia-1-azabicyclo[3.2.0]heptane-2-carboxylic acid in a 50/50 THF/water solution containing 0.1 mole of triethylamine is added to the above formed solution. This mixture is stirred for 30 minutes at −10° C. and then the temperature is raised to about 20° C. Stirring is continued for an additional 30 minutes. The pH is adjusted to 4.5 to 5.5, and the coupled product is extracted into ethyl acetate. The ethyl acetate is dried over magnesium sulfate, filtered and evaporated to give the coupled product, 6-[[(benzyloxycarbonyl)amino]-hydroxy-3-(methoxymethyl)-phenyl]acetyl]amino]-3,3-dimethyl-7-oxo-4-thia-1-azabicyclo[3.2.0]heptane-2-carboxylic acid.

The thus formed compound is added to water which contains a suspension of 30% Pd/BaCO₃ catalyst. This suspension is then treated with hydrogen gas at room temperature for 1 hour. Filtration of the aqueous solution removes the catalyst. Removal of the solvent gives the title compound.

EXAMPLE 38

6-[[[[3-(Azidomethyl)-4-hydroxyphenyl]carboxy]acetyl]-amino]-3,3-dimethyl-7-oxo-4-thia-1-azabicyclo[3.2.0]-heptane-2-carboxylic acid α-Carboxy-3-(azidomethyl)-4-hydroxybenzeneacetic acid (0.20 mole) in dry ether is treated with 0.22 mole of thionyl chloride and 1 drop of dimethylformamide. This mixture is heated at reflux for 3 hours and the solvent is removed under reduced pressure. Benzene is added to remove the last traces of thionyl chloride by codistillation at reduced pressure.

The monoacid chloride (0.10 mole) thus formed is added to dry ether. This ether solution is then added to 0.10 mole of 6-amino-3,3-dimethyl-7-oxo-4-thia-1-azabicyclo[3.2.0]heptane-2-carboxylic acid in 2/1 water/ether mixture containing 0.1 mole of sodium hydroxide, the temperature being maintained at 0° to 10° C. The mixture is stirred for 30 minutes at about 10° C. and the pH of the mixture is adjusted to about 2.5 to 3.5. The organic (ether) layer is separated from the aqueous layer. The ether is washed with water which is then discarded. The ether is again washed with water, the pH of which is adjusted to 7. Acidification of this water to a pH of 4.5 to 5.5 followed by cooling gives the title compound.

In like manner and using equivalent quantities of α-sulfo-3-(azidomethyl)-4-hydroxybenzeneacetic acid or α-carbethoxy-3-(azidomethyl)-4-hydroxybenzeneacetic acid in place of α-carboxy-3-(azidomethyl)-4-hydroxybenzeneacetic acid gives the respective penicillin derivatives: 6-[[[3-(azidomethyl)-4-hydroxyphenyl]sulfoacetyl]amino]-3,3-dimethyl-7-oxo-4-thia-1-azabicyclo[3.2.0]heptane-2-carboxylic acid; and 6-[[[3-(azidomethyl)-4-hydroxyphenyl]carbethoxyacetyl]amino]-3,3-dimethyl-7-oxo-4-thia-1-azabicyclo[3.2.0]heptane-2-carboxylic acid.

EXAMPLE 39

6-[[[(tert-Butyloxycarbonyl)amino[4-hydroxy-3-methoxymethyl)phenyl]acetyl]amino]-3,3-dimethyl-7-oxo-4-thia-1-azabicyclo[3.2.0]heptane-2-carboxylic acid α-(tert-Butyloxycarbonyl)amino[4-hydroxy-3-(methoxymethyl)benzeneacetic acid, 0.05 mole, is added to tetrahydrofuran. The temperature of the solution is maintained at −10° C. while 0.05 mole of isobutylchloroformate is added. The reaction mixture is stirred at −10° C. for about 30 minutes and then a solution of 6-amino-3,3-dimethyl-7-oxo-4-thia-1-azabicyclo[3.2.0]heptane-2-carboxylic acid in 1/1 tetrahydrofuran/water containing triethylamine (0.05 mole) is added. The temperature of the resulting reaction mixture is maintained at −10° C. for 30 minutes. Thereafter the temperature is raised to 20° C. and maintained at this temperature for 30 minutes. The organic solvent is removed, the aqueous phase is layered with ethyl acetate. The pH of the aqueous phase is adjusted to between 2.5 and 3.5. The ethyl acetate is separated from the aqueous phase and is dried over magnesium sulfate. The magnesium sulfate is removed by filtration and evaporation of the ethyl acetate gives the title compound.

NMR (DMSO-D₆) ppm (δ) 1.42 (s,9), superimposed on it 1.54 (s,3), 3.24 (s,3), 4.13 (s,1), 4.31 (s,2), 5–5.7 (m,3), 6.5–7.5 (m,3).

In like manner and using an equivalent quantity of α-(tert-butyloxycarbonyl)amino-3-(azidomethyl)-4-hydroxybenzeneacetic acid or α-(aminocarbonyl)amino[4-hydroxy-3-(thiocyanatomethyl)benzeneacetic acid in place of α-(tert-butyloxycarbonyl)amino-4-hydroxy-3-(methoxymethyl)benzeneacetic acid gives the following penicillin derivatives:

6-[[[[3-(azidomethyl)-4-hydroxyphenyl](tert-butyloxycarbonyl)amino]acetyl]amino]-3,3-dimethyl-7-oxo-4-thia-1-azabicyclo[3.2.0]heptane-2-carboxylic acid; NMR (DMSO-D₆) ppm (δ) 1.4 (superimposed s,9, s,3, s,3), 4.13 (s,1), 4.32 (s,2), 5–5.7 (m,3), 6.5–7.5 (m,3); and 6-[[(aminocarbonyl)amino[4-hydroxy-3-(thiocyanatomethyl)-phenyl]acetyl]amino]-3,3-dimethyl-7-oxo-4-thia-1-azabicyclo[3.2.0]heptane-2-carboxylic acid.

EXAMPLE 40

6-[[[3-(Azidomethyl)-4-hydroxyphenyl]hydroxyacetyl]amino]-3,3-dimethyl-7-oxo-4-thia-1-azabicyclo[3.2.0]heptane-2-carboxylic acid α-Hydroxy-3-(azidomethyl)-4-hydroxybenzeneacetic acid (30 mmole) is dissolved in tetrahydrofuran (THF). To this solution is added (45 mmole) bistrimethylsilylacetamide and (30 mmole) triethylamine. The mixture is refluxed for 2 hours after which the reaction mixture is cooled to about −10° C. and 30 mmole of isobutylchloroformate is added dropwise. After 30 mixtures at −10° C., 30 mmole of 6-amino-3,3-dimethyl-7-oxo-4-thia-1-azabicyclo [3.2.0]heptane-2-carboxylic acid in 50 ml of THF-20 ml of water containing 30 mmole of triethylamine is added to the previously prepared solution at −10° C. The temperature of the reaction mixture is allowed to warm from −10° C. to room temperature over one hour. About 50 ml of saturated sodium bicarbonate and 100 ml of water are added to the reaction mixture which is twice extracted with ether. The aqueous phase is layered with ethyl acetate and the pH is adjusted to 1.5 by the addition of hydrochloric acid. The ethyl acetate is separated from the aqueous phase, dried over sodium sulfate, filtered and evaporated to give the title compound.

EXAMPLE 41

6-[[[4-Hydroxy-3-(methoxymethyl)phenyl]acetyl]amino]-6-methoxy-3,3-dimethyl-7-oxo-4-thia-1-azabicyclo [3.2.0]-heptane-2-carboxylic acid, ethyl ester Equivalent amouts (0.05 mole) of the sodium salt of 4-hydroxy-3-(methoxymethyl)benzeneacetic acid and 6-amino-6-methoxy-3,3-dimethyl-7-oxo-4-thia-1-azabicyclo[3.2.0]-heptane-2-carboxylic acid, ethyl ester, are added to dimethylformamide (DMF). The temperature is maintained at 0° C. Then about 1.2 equivalents of dicyclohexylcarbodiimide in DMF is added. The mixture is stirred at 0° C. for from 0.5 to 3 hours and an additional 2 to 5 hours at room temperature. Filtration of the reaction mixture removes the formed dicyclohexylurea. The filtrate is then diluted with chloroform, methylene chloride or ethyl acetate, washed with water, dried and evaporated to give the title compound.

EXAMPLE 42

6-[[Amino[3-(chloromethyl)-4-hydroxyphenyl]acetyl]amino]-3,3-dimethyl-7-oxo-4-thia-1-azabicyclo[3.2.0]heptane-2-carboxylic acid α-Amino[3-(chloromethyl)-4-hydroxybenzeneacetic acid (0.01 mole) in diethyl ether is treated with anhydrous hydrogen chloride to form the amine hydrochloride salt. Then 0.011 mole of thionyl chloride is added and the resulting mixture is refluxed for 2 hours. Removal of the solvents followed by remvoal of excess thionyl chloride by codistillation with added benzene gives the acid chloride hydrochloride of α-amino [3-(chloromethyl)-4-hydroxybenzeneacetic acid.

The thus formed acid chloride hydrochloride (0.01 mole) is added to tetrahydrofuran (THF) at a temperature of between 0° and 10° C. 6-Amino-3,3-dimethyl-7-oxo-4-thia- 1-azabicyclo[3.2.0]heptane-2-carboxylic acid (0.01 mole) in THF-water mixture (2/1) containing an equivalent of triethylamine (0.01 mole) is added to the solution of the acid chloride hydrochloride in THF. This mixture is stirred for 30 minutes at 10° C. and for 30 minutes at 20° to 25° C. Water is added so as to double the volume of the reaction mixture. The THF is then removed under reduced pressure. The aqueous phase is layered with ethyl acetate prior to adjusting the pH to 4.5 to 5.5. The ethyl acetate is separated from aqueous phase, dried over magnesium sulfate, filtered and evaporated to give the title compound.

EXAMPLE 43

6-[[Amino[4-hydroxy-3-(sulfomethyl)phenyl]acetyl]amino]-3,3-dimethyl-7-oxo-4-thia-1-azabicyclo [3.2.0]heptane-2-carboxylic acid To a solution of 6-[[amino[3-(chloromethyl)-4-hydroxyphenyl]acetyl]amino]-3,3-dimethyl-7-oxo-4-thia-1-azabicyclo[3.2.2.0]heptane-2-carboxylic acid (0.05 mole) in 1:1 tetrahydrofuran/water is added 0.06 mole of sodium bisulfite. The temperature is maintained at 35° C. for 3 hours. The solvents are evaporated and the residue extracted with ethyl acetate. The ethyl acetate is dried over magnesium sulfate, filtered to remove the magnesium sulfate and then evaporated to give the title compound.

EXAMPLE 44

6-[[[3-(Azidomethyl)-4-hydroxyphenyl][](tert-butyloxycarbonyl)amino]acetyl]amino]-3,3-dimethyl-7-oxo-4-thia-1-azabicyclo[3.2.0]heptane-2-carboxylic acid; N-ethoxycarbonyl-N-methylaminomethyl ester The sodium salt of 6-[[[3-(azidomethyl)-4-hydroxyphenyl][](tert-butyloxycarbonylamino]acetyl]amino]-3,3-dimethyl-7-oxo-4-thia-1-azabicyclo[3.2.0]heptane-2-carboxylic acid (2.5 mmole of N-chloromethyl-N-methylurethane for 1 hour. The mixture is then poured into ice water and the precipitated solid is removed by filtration, and is thoroughly washed with water. The filtered solid is dissolved in ethyl acetate and washed with aqueous sodium bicarbonate and then with water. The organic layer is dried over magnesium sulfate, filtered and evaporated to give the title compound.

EXAMPLE 45

6-[[(tert-Butyloxycarbonyl)amino-[4-hydroxy-3-(thiocyanatomethyl)phenyl]acetyl]amino]-3,3-dimethyl-7-oxo-4-thia-1-azabicyclo[3.2.0]heptane-2-carboxylic acid, p-(pivaloyoxy)-benzyl ester 6-[[(tert-Butyloxycarbonyl)amino[4-hydroxy-3-(thiocyanatomethyl)phenyl]acetyl]amino]-3,3-dimethyl-7-oxo-4-thia-1-azabicyclo[3.2.0]heptane-2-carboxylic acid, sodium salt, 6.6 mole, is added to dimethylformamide with stirring. Then 2 equivalents of p-(pivaloxyloxy)benzyl alcohol is added and the mixture cooled to 0° C. To this mixture is added 7.2 mole of dicyclohexylcarbodiimide in DMF. Stirring is continued for 1 hour at 0° C. and for an additional hour at room temperature. The dicyclohexylurea formed is removed by filtration. Dilution of the reaction mixture with ethyl acetate is followed by prolonged washing with water to remove the DMF. The organic phase is dried, filtered and evaporated to give the title compound.

EXAMPLE 46

6-[[[4-Hydroxy-3-[(methylthio)methyl]phenyl]acetyl]amino]-3,3-dimethyl-
7-oxo-4-thia-1-azabicyclo[3.2.0]heptane-2-carboxylic acid,
2-(tert-butyloxycarbonyl)amino-3-methylbutyryloxymethyl ester A suspension of 5 grams of 6-[[[4-hydroxy-3-[(methylthio)methyl]phenyl]acetyl]amino]-3,3-dimethyl-7-oxo-4l-thia-1-azabicyclo[3.2.0]heptane-2-carboxylic acid, sodium salt, and 8.5 g of N-tert-butyloxycarbonyl-L-valine chloromethyl ester, prepared according to the general procedure described in W. German Offen. No. 2,236,620, are mixed in dimethylformamide (DMF) and stirred for 72 hours. The mixture is diluted with water to remove the DMF. The ethyl acetate is washed with sodium bicarbonate solution and finally with water. Drying over magnesium sulfate, removal of the magnesium sulfate by filtration and evaporation of the ethyl acetate gives the title compound.

We claim:
1. A compound of the formula

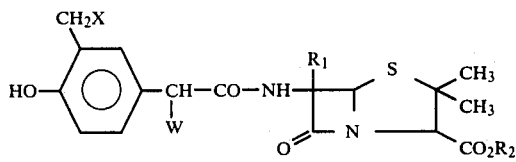

wherein W is hydrogen, hydroxy, —SO₃H or —COOR₃ wherein $R_3$ is selected from hydrogen, phenyl or 5-indanyl, an alkanoyloxymethyl group in which the alkanoyloxy group contains from 2 to 5 carbon atoms, or a 1 to 4 carbon alkyl group; —NHR₄ wherein $R_4$ is hydrogen, tert-butyloxycarbonyl,

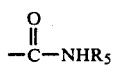

wherein $R_5$ is hydrogen, a lower alkyl group of from 1 to 4 carbon atoms or a phenyl group; X is chloro, bromo, an alkoxy group from 1 to 4 carbon atoms, an R₆—S—, R₆SO—, R₆SO₂—group wherein $R_6$ is a lower alkyl group of from 1 to 4 carbon atoms; azido; cyano; NCNH—; HSO₃—; —SCN; —OCN; CH₃SO₂NH—; isothiourea; substituted isothiourea wherein the substituents are amino, formylamino, guanylamino, a lower alkyl group of from 1 to 4 carbon atoms and concatenated alkylene groups in the form of a series of from 2 to 6 methylene groups; pyridylthio; 1-methyltetrazol-5-ylthio; 1,3,4-thiadiazol-2-ylthio; 1,3,4-triazol-2-ylthio; —SH, SSO₃H; F₃CS—;

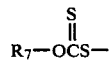

wherein $R_7$ is lower alkyl of from 1 to 4 carbon atoms;

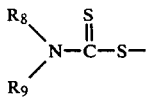

wherein $R_8$ and $R_9$ separately are hydrogen, a lower alkyl group of from 1 to 4 carbon atoms, when taken together $R_8$ and $R_9$ may form a concatenated chain of from 4 to 7 methylene groups, a concatenated chain of from 5 to 7 methylene groups wherein one of these methylene groups is replaced by an oxygen atom or an R₁₀—N group wherein $R_{10}$ is a lower alkyl group of from 1 to 4 carbon atoms, with a proviso that when X is chlorine or bromine, $R_4$ is other than a tert-butyloxycarbonyl group or a 3-ethyoxy-1-methyl-3-oxo-1-propen-1-yl group. $R_1$ is hydrogen or a methoxy group. $R_2$ is hydrogen, a straight or branched lower alkyl group of from 1 to 4 carbon atoms, a straight or branched alkanoyloxymethyl group in which the alkanoyl moiety has from 1 to 4 carbon atoms, an alkanoylaminomethyl group in which the alkanoyl moiety is straight or branched and has from 1 to 4 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, p-(alkanoyloxy)-benzyl group in which the alkanoyl moiety is straight or branched and has from 1 to 4 carbon atoms; in aminoalkanoyloxymethyl group in which the alkanoyl moiety has from 2 to 15 carbon atoms and the amine nitrogen may be mono- or di-substituted with a straight or branched lower alkyl group having from 1 to 4 carbon atoms; and pharmaceutically acceptable salts thereof.

2. A compound of claim 1 wherein $R_1$ is hydrogen or methoxy, X is other than chlorine or bromine and W is —NHR₄ wherein $R_4$ is a tert-butyloxycarbonyl group.

3. A compound of claim 2 which is 6-[[(tert-butyloxycarbonyl)amino[4-hydroxy-3-(methoxymethyl)-phenyl]acetyl]-amino]-3,3-dimethyl-7-oxo-4-thia-1-azabicyclo[3.2.0]-heptane-2-carboxylic acid or a pharmaceutically acceptable salt thereof.

4. A compound of claim 2 which is 6-[[[3-(azidomethyl)-4-hydroxyphenyl][](tert-butyloxycarbonyl)amino]-acetyl]amino]-3,3-dimethyl-7-oxo-4-thia-1-azabicyclo-[3.2.0]heptane-2-carboxylic acid or a pharmaceutically acceptable salt thereof.

5. A compound of claim 1 wherein X is as defined in claim 1 and W is —NHR₄ wherein $R_4$ is hydrogen.

6. A compound of claim 5 which is 6-[[amino[4-hydroxy-3-(methoxymethyl)phenyl]acetyl]amino]-3,3-dimethyl-7-oxo-4-thia-1-azabicyclo[3.2.0]heptane-2-carboxylic acid or a pharmaceutically acceptable salt thereof.

7. A compound of claim 5 which is 6-[[amino[3-(azidomethyl)-4-hydroxyphenyl]acetyl]amino]-3,3-dimetyl-7-oxo-4-thia-1-azabicyclo[3.2.0]heptane-2-carboxylic acid or a pharmaceutically acceptable salt thereof.

8. A compound of claim 5 which is 6-[[amino[4-hydroxymethyl-3-[(methylthio)methyl]phenyl]acetyl]amino]-3,3-dimethyl-7-oxo-4-thia-1-azabicyclo[3.2.0-]heptane-2-carboxylic acid or a pharmaceutically acceptable salt thereof.

9. A compound of claim 5 which is 6-[[amino[3-[[(ethoxythioxomethyl)thio]methyl]-4-hydroxyphenyl]acetyl]-amino]-3,3-dimethyl-7-oxo-4-thia-1-azabicyclo[3.2.0]-heptane-2-carboxylic acid or a pharmaceutically acceptable salt thereof.

10. A compound of claim 5 which is 6-[[amino[3-[(cyanoamino)methyl]-4-hydroxyphenyl]acetyl]amino]-3,3-dimethyl-7-oxo-4-thia-1-azabicyclo[3.2.0]heptane-2-carboxylic acid or a pharmaceutically acceptable salt thereof.

* * * * *